US012765838B2

(12) United States Patent
Haverinen et al.

(10) Patent No.: US 12,765,838 B2
(45) Date of Patent: Oct. 20, 2026

(54) PROCESS FOR MANUFACTURING WEARABLE RING FORM FACTOR

(71) Applicant: Oura Health Oy, Oulu (FI)

(72) Inventors: Teemu Juhani Haverinen, Oulu (FI); Mikko Latomäki, Helsinki (FI); Jukka-Tapani Mäkinen, Oulu (FI); Marko Uusitalo, Oulu (FI); Antti Lämsä, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 19/353,475

(22) Filed: Oct. 8, 2025

(65) Prior Publication Data

US 2026/0123883 A1 May 7, 2026

Related U.S. Application Data

(63) Continuation of application No. 17/903,545, filed on Sep. 6, 2022, now Pat. No. 12,440,161.

(51) Int. Cl.

| | |
|---|---|
| ***A61B 5/00*** | (2006.01) |
| ***A44C 9/00*** | (2006.01) |
| ***B29C 45/14*** | (2006.01) |
| ***H05K 5/00*** | (2006.01) |
| ***H05K 5/06*** | (2006.01) |
| *B29L 31/00* | (2006.01) |

(52) U.S. Cl.

CPC .......... *A61B 5/6826* (2013.01); *A44C 9/0053* (2013.01); *B29C 45/14065* (2013.01); *B29C 45/14311* (2013.01); *H05K 5/0086* (2013.01); *H05K 5/062* (2013.01); *B29L 2031/743* (2013.01)

(58) Field of Classification Search

CPC ............................ A61B 5/6826; A44C 9/0053

See application file for complete search history.

(56) References Cited

U.S. PATENT DOCUMENTS

| | | | | |
|---|---|---|---|---|
| 2018/0120892 | A1 | 5/2018 | Von et al. | |
| 2021/0177353 | A1 | 6/2021 | Bhagat et al. | |
| 2021/0265054 | A1 | 8/2021 | Kosman et al. | |
| 2022/0192568 | A1 | 6/2022 | Lee et al. | |
| 2024/0081012 | A1 | 3/2024 | Haverinen et al. | |
| 2026/0072471 | A1* | 3/2026 | Zou .......................... | A61B 5/00 |

* cited by examiner

*Primary Examiner* — Livius R. Cazan

(74) *Attorney, Agent, or Firm* — ArentFox Schiff LLP

(57) ABSTRACT

Methods, systems, and devices for manufacturing a wearable device are described. A method for manufacturing a wearable device may include coupling a printed circuit board (PCB) to an inner ring-shaped housing that contains a plurality of apertures by aligning a plurality of sensors of the PCB with the plurality of apertures. The method may also include coupling an outer ring-shaped housing to the inner ring-shaped housing by surrounding the inner ring-shaped housing with the outer ring-shaped housing. Additionally, the method may include injecting a filler material through an additional aperture of the outer ring-shaped housing to fill a cavity defined by the inner ring-shaped housing and the outer ring-shaped housing, filling at least a portion of the plurality of the inner ring-shaped housing with the filler material.

15 Claims, 9 Drawing Sheets

PROCESS FOR MANUFACTURING WEARABLE RING FORM FACTOR

CROSS REFERENCE

The present Application for Patent is a continuation of U.S. patent application Ser. No. 17/903,545 by Haverinen et al., entitled "PROCESS FOR MANUFACTURING WEARABLE RING FORM FACTOR," filed Sep. 6, 2022, which is assigned to the assignee hereof, and is expressly incorporated by reference herein.

FIELD OF TECHNOLOGY

The following relates to wearable devices and data processing, including a process for manufacturing a wearable ring form factor.

BACKGROUND

Some wearable devices may be configured to collect data from users including temperature data, heart rate data, and the like. In some cases, the overall structure of the wearable device may affect the accuracy of data measurements performed by the wearable device. Additionally, wearable devices may be intended to be worn full-time, and may therefore be subject to constant wear and tear. As such, there is a desire to improve the durability of wearable devices, while also enabling the wearable devices to be manufactured in an efficient and cost-effective manner.

DETAILED DESCRIPTION

Figure 1:
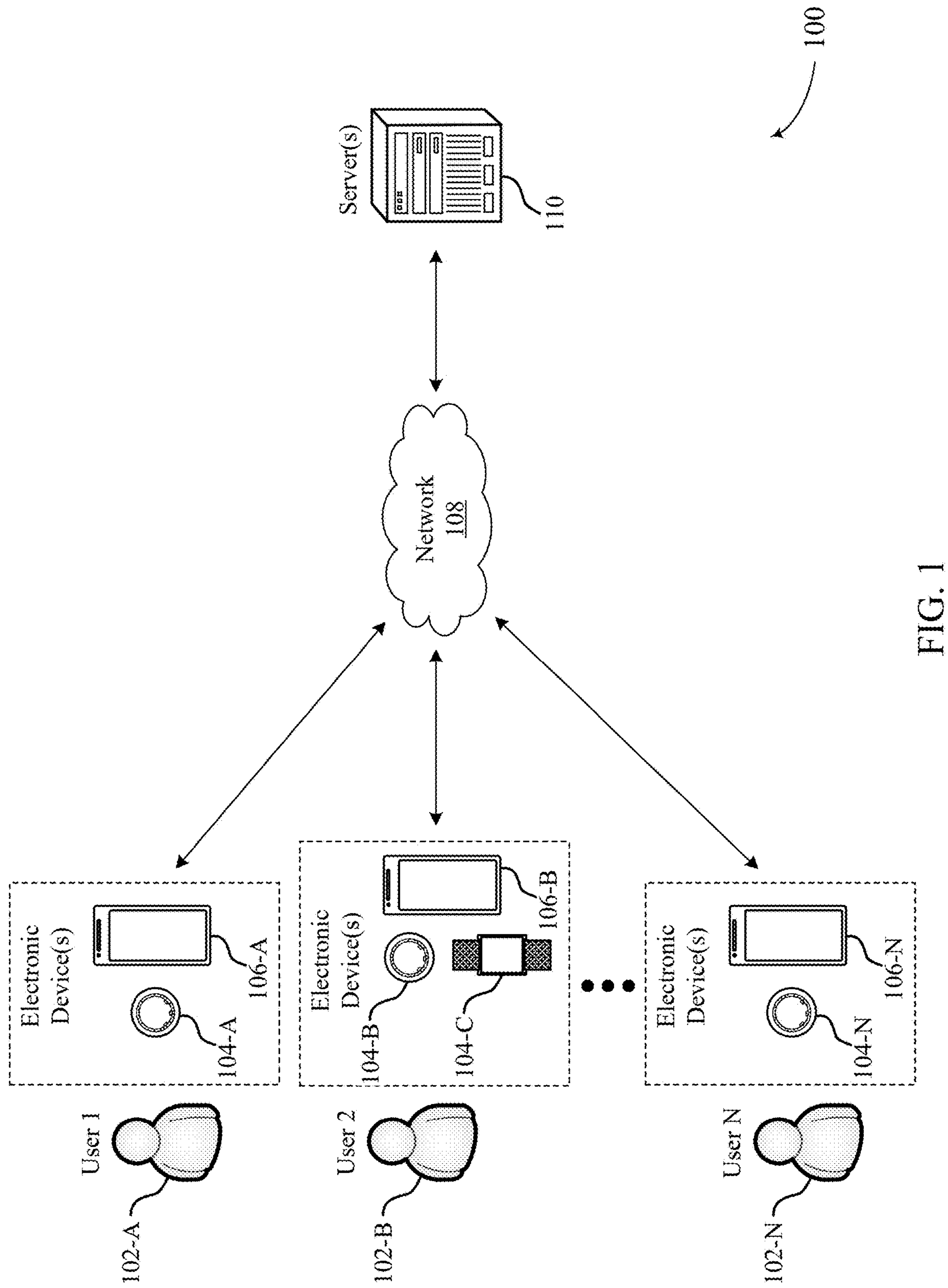
FIG. 1 illustrates an example of a system that supports a process for manufacturing wearable ring form factor in accordance with aspects of the present disclosure.

Some wearable devices may be configured to collect data from users associated with movement and other activities. For example, some wearable devices may be configured to continuously acquire physiological data associated with a user including temperature data, heart rate data, and the like. As such, some wearable devices may be configured to house one or more sensors configured to acquire physiological data from a user.

In some cases, a wearable device may collect physiological data associated with a user based on skin contact at an optical interface between sensors of the wearable device and the user's skin. In such cases, the structure of a wearable device may affect the ability of the wearable device to efficiently and accurately acquire physiological data. For example, the structure of some wearable devices may cause a loss of skin contact at the optical interface of the wearable device during the user's movement. In some examples, separate protruding domes of a wearable ring device may cause gaps between optical components of the wearable ring device and the skin of the user's finger. Such protruding domes may displace veins and arteries within the user's finger as the wearable ring device moves, causing disturbances in the signal used to collect physiological data. Because the quality of the physiological data readings is dependent on the skin contact at the optical interface of the wearable device, poor fit of the wearable device may detrimentally affect the ability of the wearable device to efficiently and accurately acquire physiological data by increasing an amount of noise in the signal. These issues with wearable devices may result in a distorted picture of the user's overall health, as well as increased power consumption and decreased user experience.

Additionally, wearable devices may be intended to be worn full-time, and may therefore be subject to constant wear and tear. As such, there is a desire to manufacture wearable devices to be durable, while also maintaining the aesthetic appeal of the wearable devices. Moreover, some wearable devices may lack individuality such that the wearable devices may include a similar design and aesthetic that lacks personalization from one wearable device to another. As such, there is a need for a manufacturing process that may be used to manufacture durable, aesthetically pleasing, and customizable wearable devices (e.g., wearable ring devices) in a cost-efficient manner.

Accordingly, aspects of the present disclosure are directed to methods for manufacturing wearable ring devices. In particular, aspects of the present disclosure are directed to techniques for improving a process for manufacturing the structure of the wearable device to facilitate improved fit and personalized design. To facilitate improved health monitoring, aspects of the present disclosure are directed to processes for manufacturing a wearable ring form factor.

In some examples, a method for manufacturing a wearable ring device may include coupling a printed circuit board (PCB) to an inner ring-shaped housing that includes a plurality of apertures. In such examples, coupling the PCB to the inner ring-shaped housing may involve aligning a plurality of sensors of the PCB with the plurality of apertures of the inner ring-shaped housing. Additionally, the method for manufacturing the wearable ring device may include coupling an outer ring-shaped housing to the inner ring-shaped housing by at least partially surrounding the inner ring-shaped housing with the outer ring-shaped housing, where the outer ring-shaped housing includes an additional aperture. In some cases, the inner and outer ring-shaped housings may be constructed of the same or different materials, such as metallic materials, epoxy materials, and the like. In some aspects, the method for manufacturing the wearable ring device may involve injecting a filler material through the additional aperture of the outer ring-shaped housing to fill a cavity that is defined at least in part by the inner ring-shaped housing and the outer housing.

In some aspects, the wearable ring devices described herein may exhibit a "comfort dome" design that provides a more even optical interface between sensors of the wearable ring device and the skin of a user. In particular, as compared to some wearable devices that include individual domes that house sensors and protrude from the inner circumference of the wearable ring device, wearable ring devices described herein may exhibit a substantially flat or slightly curved inner circumference (e.g., a comfort dome design) that improves skin contact between the wearable ring device and the user's skin and does not cause a pressure gradient inside the finger that could affect the position of internal finger structures such as veins, thereby improving robustness of physiological data measurements against optical interface and ring pressure changes.

In some aspects, the PCB of the wearable ring device may include a plurality of sensors configured to acquire physiological data from a user based on light transmitted and received through the plurality of apertures of the inner ring-shaped housing. In some examples, the epoxy material may at least partially fill the plurality of apertures of the inner ring-shaped housing. In such examples, the plurality of sensors of the PCB may be configured to acquire physiological data from the user based on the light transmitted and received through the plurality of apertures and the epoxy material. Because the inner ring-shaped housing in the comfort dome design contains apertures rather than protrusions, the structure of the inner ring-shaped housing ensures that a secure fit may be maintained during the user's movement. Additionally, the absence of protrusions (e.g., the absence of separate domes) on the inner ring-shaped housing may reduce the risk for vein movement that may be caused by a pressure gradient from the wearable ring device when worn by the user. As such, the comfort dome design of the wearable ring device may decrease an amount of noise in the signal and increase the efficiency and accuracy of the signal, contributing to a refined picture of the user's overall health. Additionally, the comfort dome design may be more comfortable for the user due to the improved fit of the wearable ring device, contributing to improved user experience.

Moreover, in some implementations, the inner ring-shaped housing may include a first metallic material, and the outer ring-shaped housing may include a second metallic material. The first metallic material and the second metallic material may be different materials or the same material. In some cases, the outer ring-shaped housing may be personalized from a variety of metallic materials, colors, designs, functionality, or a combination thereof. Additionally, or alternatively, the user may have the ability to easily change the outer ring-shaped housing (e.g., inserts or covers associated with the outer ring-shaped housing). As such, the structure of the wearable ring device as described herein provides added personalized design and aesthetics to the wearable ring device, thereby improving user experience with the wearable ring device.

Aspects of the disclosure are initially described in the context of systems supporting physiological data collection from users via wearable devices. Additional aspects of the disclosure are described in the context of example ring wearable systems, assemblies, cross sections, and manufacturing processes. Although many of the examples of a wearable device depicted herein are ring-shaped wearable devices, it should be understood that the structures described herein may also be used with wearable devices of other form factors such as watches, patches, and the like.

FIG. 1 illustrates an example of a system 100 that supports process for manufacturing wearable ring form factor in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

To perform the operations described herein, a wearable device 104 may be manufactured and assembled such that leakage of stray light is reduced and customizability is improved. According to the techniques described herein, a process for manufacturing the wearable device 104 may include aligning sensors of a PCB with apertures of an inner ring-shaped housing, surrounding the inner ring-shaped housing with an outer ring-shaped housing, and injecting a filler material through an aperture of the outer ring-shaped housing to fill a cavity defined by the inner ring-shaped housing and the outer ring-shaped housing. Due to the absence of protruding domes at the interface of the inner ring-shaped housing and skin tissue of a user, the wearable device 104 may be more comfortable to the user and optical contact may be improved. Additionally, the outer ring-shaped housing of the wearable device 104 may be exchangeable or customizable to the user's desires.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
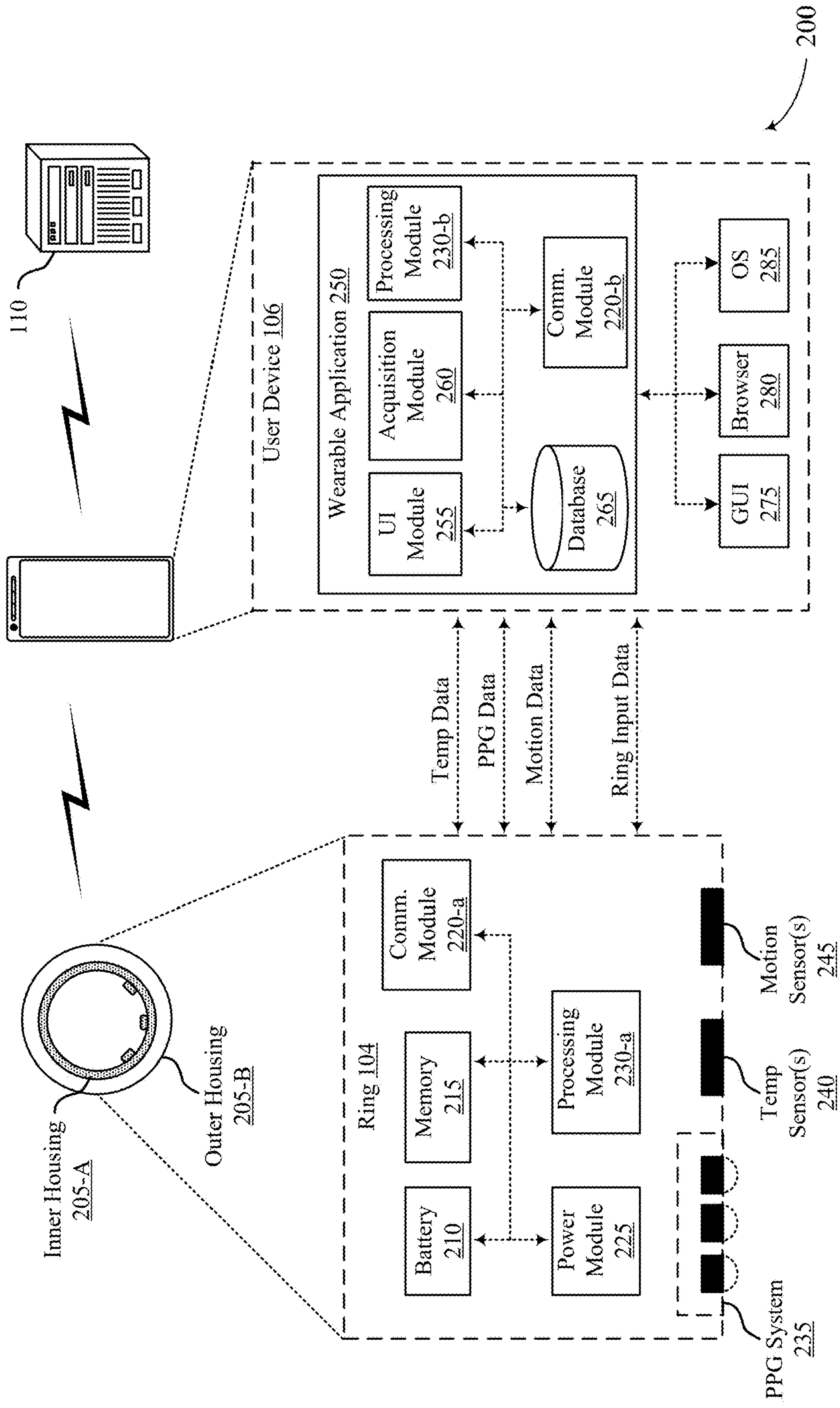
FIG. 2 illustrates an example of a system that supports the process for manufacturing wearable ring form factor in accordance with aspects of the present disclosure.

FIG. 2 illustrates an example of a system 200 that supports process for manufacturing wearable ring form factor in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more PCBs (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The “sleep” contributor may refer to the combined Sleep Score of all sleep periods within the sleep day. The “sleep balance” contributor may refer to a cumulative duration of all sleep periods within the sleep day. In particular, sleep balance may indicate to a user whether the sleep that the user has been getting over some duration of time (e.g., the past two weeks) is in balance with the user’s needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user’s sleep needs are being met. The “resting heart rate” contributor may indicate a lowest heart rate from the longest sleep period of the sleep day (e.g., primary sleep period) and/or the lowest heart rate from naps occurring after the primary sleep period.

Continuing with reference to the “contributors” (e.g., factors, contributing factors) of the Readiness Score, the “HRV balance” contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The “recovery index” contributor may be calculated based on the longest sleep period. Recovery index measures how long it takes for a user’s resting heart rate to stabilize during the night. A sign of a very good recovery is that the user’s resting heart rate stabilizes during the first half of the night, at least six hours before the user wakes up, leaving the body time to recover for the next day. The “body temperature” contributor may be calculated based on the longest sleep period (e.g., primary sleep period) or based on a nap happening after the longest sleep period if the user’s highest temperature during the nap is at least 0.5° C. higher than the highest temperature during the longest period. In some aspects, the ring may measure a user’s body temperature while the user is asleep, and the system 200 may display the user’s average temperature relative to the user’s baseline temperature. If a user’s body temperature is outside of their normal range (e.g., clearly above or below 0.0), the body temperature contributor may be highlighted (e.g., go to a “Pay attention” state) or otherwise generate an alert for the user.

In some aspects, the system 200 may support techniques for manufacturing that allow for components of the wearable ring device 104 to be housed within apertures of an inner ring-shaped housing rather than separate domes protruding from the inner ring-shaped housing, providing for improved optical contact and improved user experience. For example, a manufacturing process may include aligning sensors of a PCB with apertures of the inner ring-shaped housing, surrounding an inner ring-shaped housing with an outer ring-shaped housing, and injecting a filler material through an aperture of the outer ring-shaped housing to fill a cavity defined at least partially by the inner ring-shaped housing and the outer ring-shaped housing.

Figure 3A:
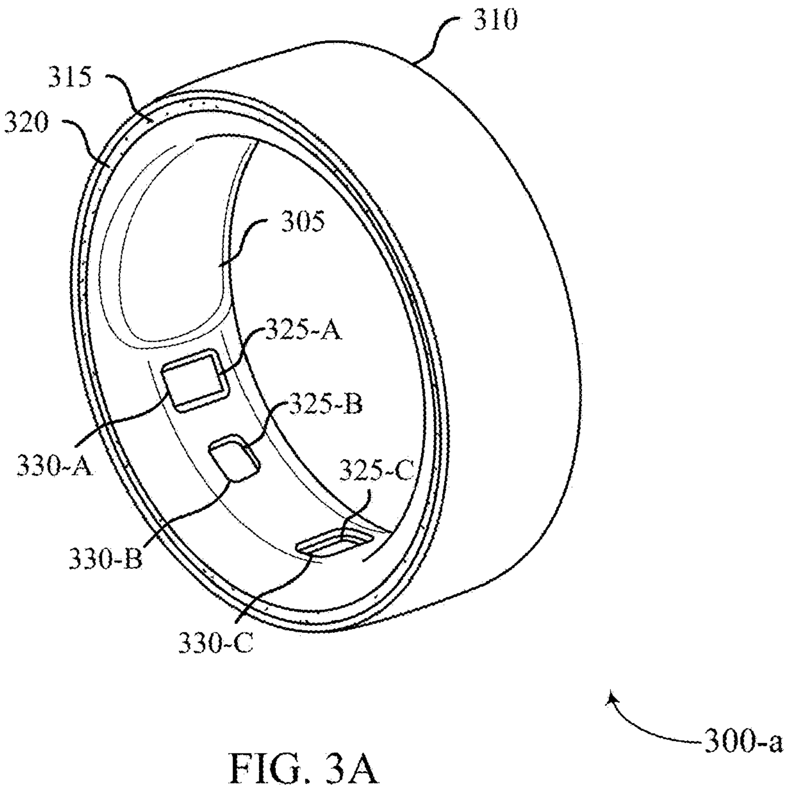
FIG. 3A illustrates an example of a ring wearable system that supports the process for manufacturing a wearable ring form factor in accordance with aspects of the present disclosure.

FIG. 3A illustrates an example of a ring wearable system 300-*a* that supports a process for manufacturing a wearable ring form factor in accordance with aspects of the present disclosure. The ring wearable system 300-*a* may be an example of a wearable device 104 or a ring 104 as described with reference to FIGS. 1 and 2. The ring wearable system 300-*a* may include an inner ring-shaped housing 305, an outer ring-shaped housing 310, and a PCB located between the inner ring-shaped housing 305 and the outer ring-shaped housing 310. In some aspects, the PCB may be contained within the boundaries of the inner ring-shaped housing 305 such that sensors 330 of the PCB align with a plurality of apertures 325, or cavities, of the inner ring-shaped housing 305 without compromising the fit of the ring wearable system 300-*a*.

For instance, the ring wearable system 300-*a* may include an inner ring-shaped housing 305 constructed from a first material (e.g., a first metallic material), and an outer ring-shaped housing 310 constructed from a second material (e.g., a second metallic material). The first material of the inner ring-shaped housing 305 and the second material of the outer ring-shaped housing 310 may be selected from a variety of materials, such as metal, plastic, carbon fiber, ceramic, zirconium, and the like. Additionally, the second material of the outer ring-shaped housing 310 may be the same or different from the first material of the inner ring-shaped housing 305. The inner ring-shaped housing 305 may be manufactured separately from the outer ring-shaped housing 310. As such, the inner ring-shaped housing 305 or the outer ring-shaped housing 310 may be separately configured or exchanged from the ring wearable system 300-*a*, providing added customizability to the user’s tastes. For example, the inner ring-shaped housing 305 may be constructed from carbon fiber, and the outer ring-shaped housing 310 may be constructed from stainless steel.

In the ring wearable system 300-*a*, the PCB may be coupled to the inner ring-shaped housing 305. For instance, the PCB may include a plurality of sensors 330 disposed along the interior surface of a PCB and configured to sense physiological data for a user by interfacing with the user’s skin. To couple the PCB to the inner ring-shaped housing 305, the sensors 330 of the PCB may be positioned within the inner ring-shaped housing 305 such that the sensors 330 align with the apertures 325. For example, the sensor 330-*a* may align with the aperture 325-*a*, the sensor 330-*b* may align with the aperture 325-*b*, and the sensor 330-*c* may align with the aperture 325-*c*. Sensors 330 of the PCB may include, but are not limited to, LEDs, photodetectors, accelerometers, temperature sensors, and the like.

The outer ring-shaped housing 310 may be coupled to the inner ring-shaped housing 305 by at least partially surrounding the inner ring-shaped housing 305. In some examples, the outer ring-shaped housing 310 may be coupled to the inner ring-shaped housing 305 with a sealing material 320, such as an adhesive (e.g., epoxy, polyurethane adhesive, polyimide adhesive), a welding material (e.g., aluminum, steel, iron, copper, nickel), a compression fit component, or the like. In such examples, the sealing material 320 may bind the outer ring-shaped housing 310 to the inner ring-shaped housing 305. The sealing material 320 may prevent stray light emitted from one or more of the sensors 330 (e.g., LEDs) from leaking away from the intended optical path. For instance, the ring wearable system 300-*a* may utilize one or more LEDs (e.g., red LEDs, green LEDs) on the PCB to collect physiological data based on arterial blood flow within the user’s finger. To provide for accurate physiological data, light emitted from the one or more LEDs may be directed along an optical path that passes through a user’s finger tissue. Light emitted from the one or more LEDs that strays from the intended optical path may be referred to as stray light. As such, the ring wearable system 300-*a* may acquire physiological data that more accurately represents the health of the user by minimizing the amount of stray light escaping the intended optical path. The sealing material 320 may prevent any stray light from escaping the ring wearable system 300-*a*. As such, stray light that escapes the intended optical path may be redirected to the finger tissue by bouncing from the sealing material 320 if the sealing material 320 is reflective. Additionally, or alternatively, light that escapes the intended optical path may be absorbed by the sealing material 320 if the sealing material 320 is absorptive.

A cavity 315 of the ring wearable system 300-*a* may at least partially be defined by the inner ring-shaped housing 305 and the outer ring-shaped housing 310. As such, the cavity 315 may occupy the space located between the inner ring-shaped housing 305 and the outer ring-shaped housing 310. In some aspects, the method for manufacturing the ring wearable system 300-*a* may include sliding the PCB within a groove of the inner ring-shaped housing 305 such that the PCB resides in the cavity 315 and the sensors 330 align with the apertures 325. This will be further shown and described in the context of FIG. 5A.

In some cases, air gaps between the sensors 330 and the finger tissue of the user may contribute to inaccurate PPG and SpO2 measurements. To provide a better optical interface between the sensors 330 and finger tissue of the user and improve the fit of the ring wearable system 300-*a*, the process for manufacturing the ring wearable system 300-*a* may include filling at least a portion of the plurality of apertures 325 with the filler material. For example, a filler material may be injected through an additional aperture of the outer ring-shaped housing 310 to fill the cavity 315 defined by the inner ring-shaped housing 305 and the outer ring-shaped housing 310. By injecting the filler material into the cavity 315, the filler material may fill one or more of the apertures 325. In some examples, the filler material may be filled, polished, or both, such that the filler material is flush with the inner circumferential surface of the inner ring-shaped housing 305, forming the substantially flat or slightly curved inner circumferential surface (e.g., comfort dome design). Due to the absence of protruding domes in the comfort dome design, the wearable ring device may result in pressure being more evenly applied across the user's skin, thereby reducing or eliminating changes in physiology of the user's finger (e.g., evenly applied pressure may reduce or eliminate displacements of the user's veins and arteries within the finger).

Figure 3B:
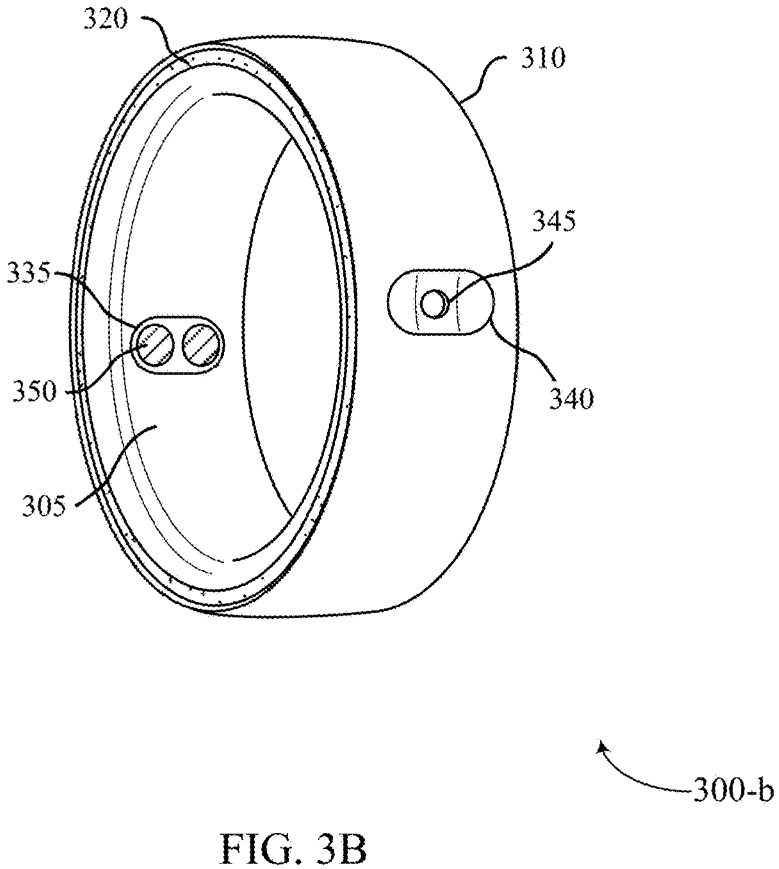
FIG. 3B illustrates an example of a ring wearable system that supports the process for manufacturing a wearable ring form factor in accordance with aspects of the present disclosure.

FIG. 3B illustrates an example of a ring wearable system 300-*b* that supports a process for manufacturing a wearable ring form factor in accordance with aspects of the present disclosure. The ring wearable system 300-*b* may include the inner ring-shaped housing 305, the outer ring-shaped housing 310, and the PCB located between the inner ring-shaped housing 305 and the outer ring-shaped housing 310, as described with reference to FIG. 3A. In some aspects, the ring wearable system 300-*b* may be manufactured by injecting the filler material through an additional aperture 345 of the outer ring-shaped housing 310 to fill the cavity 315, simplifying the manufacturing process for the ring wearable system 300-*b*. In additional or alternative implementations, the filler material may be injected through one or more of the apertures 325 of the inner ring-shaped housing 305.

The additional aperture 345 may be a hole that cuts through the outer ring-shaped housing 310. In some examples, the additional aperture 345 may be located on the side of the ring wearable system 300-*b* that is opposite from the charging component(s) 350 of the ring wearable system 300-*b*. For instance, the additional aperture 345 may be located at a filling portion 340 on a first side of the ring wearable system 300-*b*, and the charging component(s) 350 may be located at a charging portion 335 on a second side of the ring wearable system 300-*b* that is opposite from the first side. In some cases, as shown in FIG. 3B, the additional aperture 345 may be located within a cavity or detent within the outer ring-shaped housing 310.

The process for manufacturing the ring wearable system 300-*b* may involve filling at least a portion of the plurality of apertures 325 of the inner ring-shaped housing 305 with the filler material by injecting the filler material through the additional aperture 345 of the outer ring-shaped housing 310. In other words, the filler material may be injected through the outer ring-shaped housing 310 so that the filler material at least partially fills a cavity of the wearable ring device and extrudes from the apertures 325 of the inner ring-shaped housing 305.

To enable transmission of light through the plurality of apertures 325, the filler material may include a transparent epoxy material. As such, light emitted from LEDs of the PCB may travel through the filler material, pass through the apertures 325, and penetrate the finger tissue. Additionally, the light that penetrated the finger tissue may travel from the finger tissue to the sensors 330 (e.g., photodetectors) of the PCB by passing through the apertures 325 and the filler material once again. The filler material may act as a light concentrator for the ring wearable system 300-*b*. As such, more light emitted from LEDs may travel along the intended optical paths.

Figure 4:
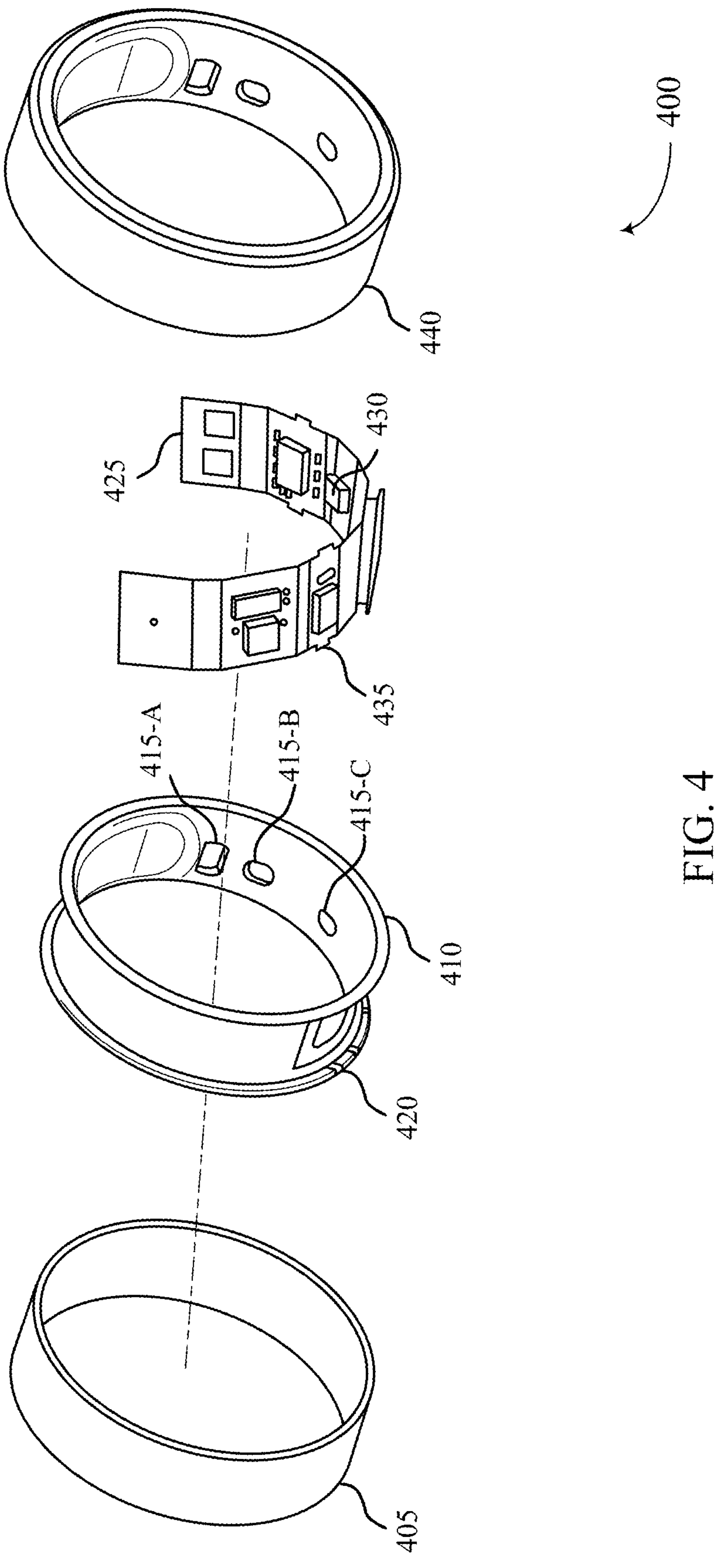
FIG. 4 illustrates an example of a ring wearable assembly that supports the process for manufacturing a wearable ring form factor in accordance with aspects of the present disclosure.

FIG. 4 illustrates an example of a ring wearable assembly 400 that supports process for manufacturing wearable ring form factor in accordance with aspects of the present disclosure. The ring wearable assembly 400 may include separate parts that are individually manufacturable. As such, each part of the ring wearable assembly 400 may be customized or exchanged without compromising efficiency to manufacture the wearable ring device in its entirety.

For example, the ring wearable assembly 400 may include an outer ring-shaped housing 405, an inner ring-shaped housing 410, and a PCB 425. The inner ring-shaped housing 410 may be constructed from a first material (e.g., a first metallic material), and the outer ring-shaped housing 405 may be constructed from a second material (e.g., a second metallic material) that is the same or different from the first material. The respective components of the ring wearable assembly 400 may be examples of the corresponding components shown and described in FIG. 3.

In some examples, the outer ring-shaped housing 405 may act as an outer cover for the ring wearable assembly 400, where the outer ring-shaped housing 405 is fixed or semi-fixed. For instance, the outer ring-shaped housing 405 may be fixed such that the outer ring-shaped housing 405 is determined by a ring supplier. In some cases, the ring supplier may manufacture a classic outer cover (e.g., a full metal outer cover) for a fixed outer ring-shaped housing 405. In some other cases, the ring supplier may manufacture an active decoration master frame and an associated active style decoration piece, where the active decoration master frame has an internal geometry similar to the classic outer cover. Alternatively, the outer ring-shaped housing 405 may be semi-fixed or changeable such that a decoration piece of the outer ring-shaped housing 405 can be changed by a user, a ring supplier, or some other external source. For instance, a supplier associated with a brand different from the ring supplier may manufacture a branding cover for a semi-fixed outer ring-shaped housing 405 that is not provided by the ring supplier. The color or material of the outer ring-shaped housing 405 may be selected from a wide array of colors or materials.

The inner ring-shaped housing 410 may include a metal or non-metal inlet for the ring wearable assembly 400. The inner ring-shaped housing 410 may be manufactured via an metal insert molding process or a non-metal insert molding process. In some examples, the inner ring-shaped housing 410 may include a plurality of apertures 415 (e.g., apertures 415-*a*, 415-*b*, and 415-*c*).

In some implementations, the inner ring-shaped housing 410 may include components or features that help orient the PCB 425 in the correct radial orientation within the inner ring-shaped housing 410. For example, the inner ring-shaped housing 410 may include a first set of locating components 420 (e.g., detents, grooves, protrusions, or the like) along the inner edges of the inner ring-shaped housing 410. Additionally, or alternatively, the inner ring-shaped housing 410 may include flanges along the edges of the inner ring-shaped housing 410, where the first set of locating components 420 are located on the inner edges of the flanges (as illustrated). In some examples, the inner ring-shaped housing 410 may be elliptical shaped in order to prevent unintentional rotation during finger movement.

The PCB 425 may be a flexible PCB that includes a plurality of sensors or electrical components (e.g., a sensor 430). In some examples, the plurality of sensors may be positioned asymmetrically within the PCB 425. For example, the sensors on the PCB 425 may include a first light-emitting component (e.g., a first LED) positioned relative to the inner ring-shaped housing 410 at a first radial position, a second light-emitting component (e.g., a second LED) positioned relative to the inner ring-shaped housing 410 at a second radial position, and a third light-emitting component (e.g., a third LED) positioned relative to the inner ring-shaped housing 410 at a third radial position. If the sensors are positioned asymmetrically, the first radial position and the third radial position may define a segment of the inner ring-shaped housing 410 between the first radial position and the second radial position, where the third radial position is different from a radial midpoint of the segment.

In some examples, the PCB 425 may include a second set of locating components 435 (e.g., detents, grooves, protrusions, or the like) that are configured to interface with the set of locating components 420 of the inner ring-shaped housing 410. The second set of locating components 435 may be located on the edges of the PCB 425. If the first set of locating components 420 of the inner ring-shaped housing 410 include one or more protrusions, the second set of locating components 435 of the PCB 425 may include one or more grooves or detents. Additionally, or alternatively, if the first set of locating components 420 of the inner ring-shaped housing 410 include one or more grooves or detents, the second set of locating components 435 of the PCB 425 may include one or more protrusions.

The ring wearable device 440 shown in FIG. 4 may illustrate the final form of the ring wearable assembly 400, including the outer ring-shaped housing 405, the inner ring-shaped housing 410, and the PCB 425. In order to produce the ring wearable device 440, the manufacturing process may include coupling the PCB 425 to the inner ring-shaped housing 410 by aligning the sensors of the PCB 425 with the plurality of apertures 415 of the inner ring-shaped housing 410. In some examples, the sensors of the PCB 425 may be aligned with the plurality of apertures 415 of the inner ring-shaped housing 410 based on engaging the first set of locating components 420 of the inner ring-shaped housing 410 with the second set of locating components 435 of the PCB 425. For instance, the PCB 425 may be maintained in a radial orientation of a plurality of radial orientations relative to the inner ring-shaped housing 410 by engaging the first set of locating components 420 with the second set of locating components 435. In some examples, the first set of locating components 420 may be engaged with the second set of locating components 435 based on sliding the PCB 425 within a groove of the inner ring-shaped housing 410. For example, the PCB 425 may slide within a groove of the inner ring-shaped housing 410 until the locating components 420 engage with the locating components 435. Once the locating components 420 are engaged with the locating components 435, the sensors of the PCB 425 may align with the apertures 415 of the inner ring-shaped housing 410. For instance, the sensor 430 may align with the aperture 415-*b*.

The manufacturing process may also include coupling the outer ring-shaped housing 405 to the inner ring-shaped housing 410 by at least partially surrounding the inner ring-shaped housing 410 with the outer ring-shaped housing 405. In some examples, the outer ring-shaped housing 405 may be coupled, or attached, to the inner ring-shaped housing 410 with a sealing material (e.g., an adhesive, a welding material, a compression fit component, or the like). Additionally, or alternatively, the outer ring-shaped housing 405 may be coupled, or attached, to the inner ring-shaped housing 410 based on a filler material that may be injected into the ring wearable device 440 through an aperture of the outer ring-shaped housing 405. In other words, in some implementations, the filler material may be configured to bind the outer ring-shaped housing 405 to the PCB 425 and/or the inner ring-shaped housing 410.

Figure 5A:
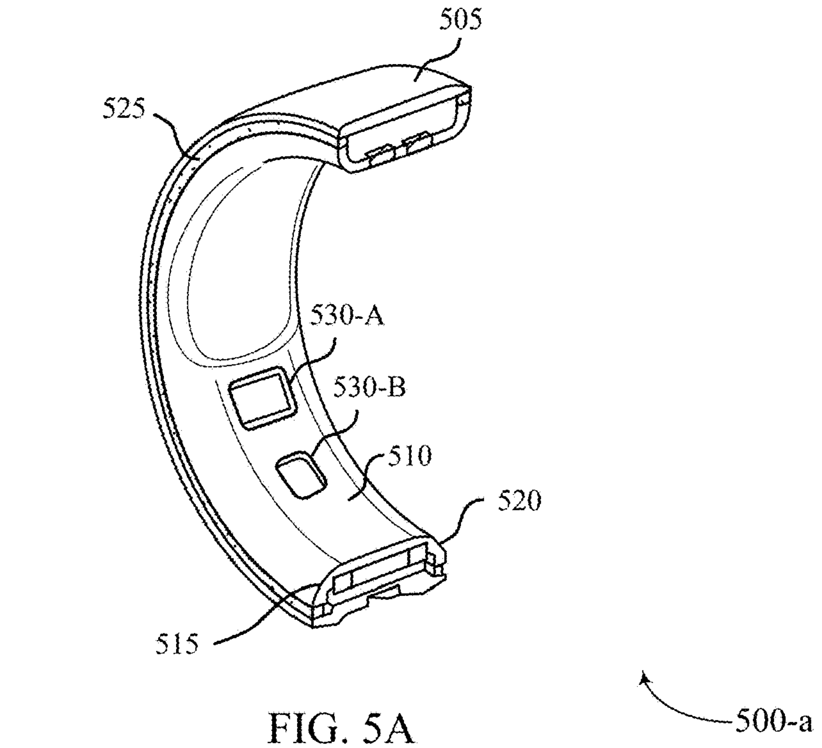
FIGS. 5A and 5B illustrate examples of ring wearable cross sections that support the process for manufacturing a wearable ring form factor in accordance with aspects of the present disclosure.

FIG. 5A illustrates an example of a ring wearable cross section 500-*a* that supports a process for manufacturing a wearable ring form factor in accordance with aspects of the present disclosure. The ring wearable cross section 500-*a* depicts the comfort dome design of the ring wearable device and system described with reference to FIGS. 3A, 3B, and 4. In particular, the ring wearable cross section 500-*a* illustrates the substantially flat (or slightly curved) cross section of the inner circumferential surface of the wearable ring device that is configured to interface with the user's finger. In this regard, the "comfort dome" shape of the wearable ring device may not include separate domes, thereby allowing for a more even optical interface surface to the skin of a user, and reducing signal disturbances that contribute to interrupted or inaccurate PPG and SpO2 measurements.

For instance, some wearable devices may include protruding domes made of epoxy that are located on top of optoelectronic components (e.g., sensors of a PCB), where the protruding domes may create steep light incidence angles in the epoxy and skin-to-air interface while also improving skin contact by protruding into the somewhat elastic skin. However, with separate domes on top of the optoelectronic components, there is a risk of losing some skin contact and affecting the finger's internal vein position when there is movement of the finger. In other words, as the wearable ring device moves, the protruding domes may displace veins and arteries within the finger, thereby changing the physiology of the finger and disturbing physiological measurements performed by the wearable ring device.

As such, the "comfort dome" design shown and described in FIG. 5A may exhibit a flat or slightly domed cross section of the inner circumferential surface that reduces the risk for signal disturbances caused by loss of skin contact, and which may lead to a more comfortable fit as compared to wearable ring devices that exhibit separate protruding domes.

For example, the ring wearable device may include the inner ring-shaped housing 510 and an outer ring-shaped housing 505. In some aspects, the inner ring-shaped housing 510 may include a first ring-shaped edge 515 and a second ring-shaped edge 520 opposite the first ring-shaped edge 515, where the inner circumferential surface of the inner ring-shaped housing 510 is flat or dome-shaped between the first ring-shaped edge 515 and the second ring-shaped edge 520. In such aspects, the inner surface of the inner ring-shaped housing 510 that contacts the user's finger is dome-shaped and capable of contacting the skin of the user's finger with a more even pressure gradient. Additionally, the ring wearable device may have a tighter, improved fit onto the user's finger, with a decreased risk of loss of skin contact when impacted by motion artifacts. Further, a dome-shaped inner circumferential surface is less complex than an inner circumferential surface that has multiple individual domes, thereby simplifying the manufacturing process for the ring wearable device.

Apertures 530 (e.g., aperture 530-*a*, aperture 530, and other apertures) may be included within the inner circumferential surface of the inner ring-shaped housing 510. In some examples, a sealing material 525 may lock the outer ring-shaped housing 505 to the inner ring-shaped housing 510. In some cases, as described herein, the sealing material may include an epoxy, a welding material, a pressure-fit component, and the like. Additionally, or alternatively, the sealing material 525 may include the filler material that is injected into the cavity of the wearable ring device.

Figure 5B:
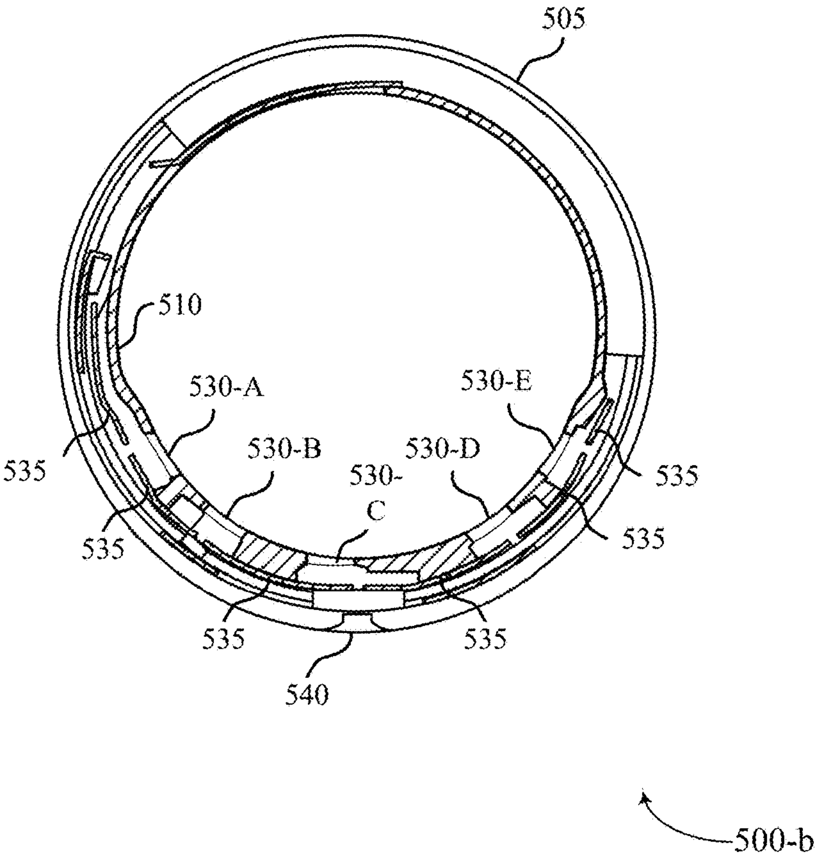

FIG. 5B illustrates an example of a ring wearable cross section 500-*b* that supports a process for manufacturing a wearable ring form factor in accordance with aspects of the present disclosure. The ring wearable cross section 500-*b* depicts a PCB 535 positioned within an internal cavity of the ring wearable device and system described with reference to FIGS. 3A, 3B, and 4, illustrating the PCB 535 coupled to the inner ring-shaped housing 510. By positioning the PCB 535 in the cavity defined by the inner ring-shaped housing 510 and the outer ring-shaped housing 505 as illustrated in the ring wearable cross section 500-*b*, sensors of the PCB 535 may be contained within the confines of the inner circumference of the inner ring-shaped housing 510.

The inner ring-shaped housing 510 may include a first set of locating components, and the PCB 535 may have a second set of locating components. The PCB 535 may be coupled to the inner ring-shaped housing 510 by engaging the first set of locating components with the second set of locating components. For instance, if the first set of locating components of the inner ring-shaped housing 510 include protrusions and the second set of locating components of the outer ring-shaped housing 505 include detents, the PCB 535 may be coupled to the inner ring-shaped housing 510 by engaging the protrusions of the inner ring-shaped housing 510 with the detents of the PCB 535. Additionally, or alternatively, if the first set of locating components of the inner ring-shaped housing 510 include detents and the second set of locating components of the outer ring-shaped housing 505 include protrusions, the PCB 535 may be coupled to the inner ring-shaped housing 510 by engaging the detents of the inner ring-shaped housing 510 with the protrusions of the PCB 535.

In some cases, the inner ring-shaped housing 510 may include a groove used for sliding the PCB 535 into the inner ring-shaped housing 510. In such cases, the PCB 535 may be slid against a groove of the inner ring-shaped housing 510 until the first set of locating components associated with the inner ring-shaped housing 510 are engaged with the second set of locating components associated with the PCB 535. For example, the PCB 535 may be slid into the groove of the inner ring-shaped housing 510 until protruding locating components of the PCB 535 are engaged with catches of the inner ring-shaped housing 510, or vice versa.

The inner ring-shaped housing 510 may include a plurality of apertures 530 (e.g., apertures 530-*a*, 530-*b*, 530-*c*, 530-*d*, and 530-*e*). The apertures 530 may act as pathways from the PCB 535 of the ring wearable device to finger tissue when worn by the user. In some examples, sensors of the PCB 535 may align with the apertures 530 of the inner ring-shaped housing 510 such that the sensors may transmit or receive signals (e.g., light) to or from the finger tissue through the apertures 530. In some examples, the location of the apertures 530 may be based on the location of the sensors on the PCB 535. For instance, if the location of the sensors is predefined and fixed on the PCB 535, the apertures 530 may be cut into the inner ring-shaped housing 510 such that the apertures 530 align with the sensors on the inner ring-shaped housing 510. Additionally, or alternatively, the location of the sensors on the PCB 535 may be based on the location of the apertures 530. For instance, if the location of the apertures 530 is predefined and fixed on the PCB 535, the PCB 535 may position the sensors on the inner ring-shaped housing 510 such that the sensors align with the apertures 530.

The sensors may be of any quantity and distributed along the PCB 535 at any assortment of locations. That is, the sensors on the PCB 535 may vary in quantity and be spread through the ring wearable device on the PCB 535. As such, the quantity and positioning of the apertures 530 may not be limited to that of apertures 530-*a*, 530-*b*, 530-*c*, 530-*d*, and 530-*e*. Additionally, or alternatively, the quantity and positioning of the sensors on the PCB 535 may be variable.

In some examples, the outer ring-shaped housing 505 may include an aperture 540 that is used to inject a filler material into the aperture 540 to at least partially fill a cavity and the apertures 530 of the wearable ring device. In other examples, the filler material may be injected into one or more of the apertures 530 of the inner ring-shaped housing 510. The methods for injecting the filler material into at least a portion of the apertures 530 may be described with reference to FIGS. 6A and 6B.

In some implementations, the material of the inner ring-shaped housing may improve an overall quality of physiological measurements collected by the inner ring-shaped housing. For example, in cases where the inner ring-shaped housing 510 includes a metallic material, the metallic material may help reflect light back into the finger tissue of the user, which may improve a signal quality, perfusion, or both, of the wearable ring device.

Figure 6A:
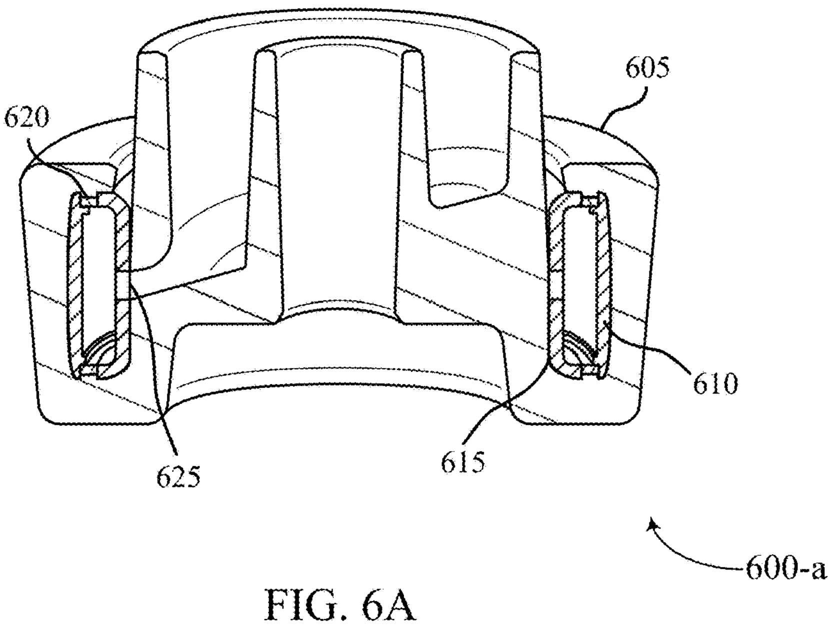
FIGS. 6A and 6B illustrate examples of inner aperture injection systems that support the process for manufacturing a wearable ring form factor in accordance with aspects of the present disclosure.

FIG. 6A illustrates an example of an inner aperture injection system 600-*a* that supports a process for manufacturing a wearable ring form factor in accordance with aspects of the present disclosure. The inner aperture injection system 600-*a* depicts a mold 605 in which a wearable ring device may be placed so that filler material may be injected into one or more cavities of the wearable ring device. By injecting the filler material into cavities of the wearable ring device, the wearable ring device may be sealed to prevent particles (e.g., liquids, dirt, and the like) from entering optical pathways of the wearable ring device, thereby preventing signal disturbances that may be caused by such particles.

As described with reference to FIGS. 3A, 3B, 4, 5A, and 5B, the wearable ring device may include an inner ring-shaped housing 615, an outer ring-shaped housing 610, and a PCB coupled to the inner ring-shaped housing 615. The outer ring-shaped housing 610 may be coupled to the inner ring-shaped housing 615, and a cavity may be defined by the outer ring-shaped housing 610 and the inner ring-shaped housing 615. In some examples, the outer ring-shaped housing 610 may be coupled to the inner ring-shaped housing 615 with a sealing material 620, sealing the cavity of the wearable ring device. The outer ring-shaped housing 610 may be coupled to the inner ring-shaped housing 615 with the sealing material before or after placing the wearable ring device into the mold 605. Additionally, or alternatively, outer ring-shaped housing 610 may be coupled to the inner ring-shaped housing 615 with a filler material.

In the inner aperture injection system 600-*a*, the wearable ring device may be placed within the mold 605 based on coupling the outer ring-shaped housing 610 to the inner ring-shaped housing 615. When placing the wearable ring device within the mold 605, the wearable ring device may be positioned such that an inner aperture 625 of the inner ring-shaped housing 615 aligns with an opening of the mold 605 used to inject the filler material. In some examples, the inner aperture 625 may be an aperture on the inner ring-shaped housing 615 that is associated with an optical component of the wearable ring device (e.g., an aperture in alignment with a sensor on the PCB of the wearable ring device). In other examples, the inner aperture 625 may be an aperture on the inner ring-shaped housing 615 that is different from the apertures associated with optical components of the wearable ring device.

When the wearable ring device is placed and properly positioned in the mold 605, a filler material may be injected through the inner aperture 625 to fill at least a portion of the plurality of apertures of the inner ring-shaped housing 615. Additionally, or alternatively, the filler material may be injected through the inner aperture 625 to at least partially fill the cavity defined by the inner ring-shaped housing 615 and the outer ring-shaped housing 610. The filler material may be selected from a variety of materials enabling transmission of light (e.g., transparent or semi-transparent epoxy). Accordingly, sensors on the PCB within the wearable ring device may transmit and receive light through the filler material medium.

The mold 605 may be used to fill apertures of inner ring-shaped housing 615 with different techniques. For instance, in some examples, the filler material may be used to fill an entirety of the apertures so that the filler material is flush with an inner circumferential surface of the inner ring-shaped housing 615. In such examples, the filler material may fill the apertures of the inner ring-shaped housing 615 to form a smooth inner surface of the wearable ring device that contacts the user's finger. In other examples, the filler material may extend beyond an inner circumferential surface of the inner ring-shaped housing 615. In such cases, the inner circumferential surface of the inner ring-shaped housing 615 may be polished to smoothen the filler material within the so that the filler material is flush with the inner circumferential surface of the inner ring-shaped housing 615.

Figure 6B:
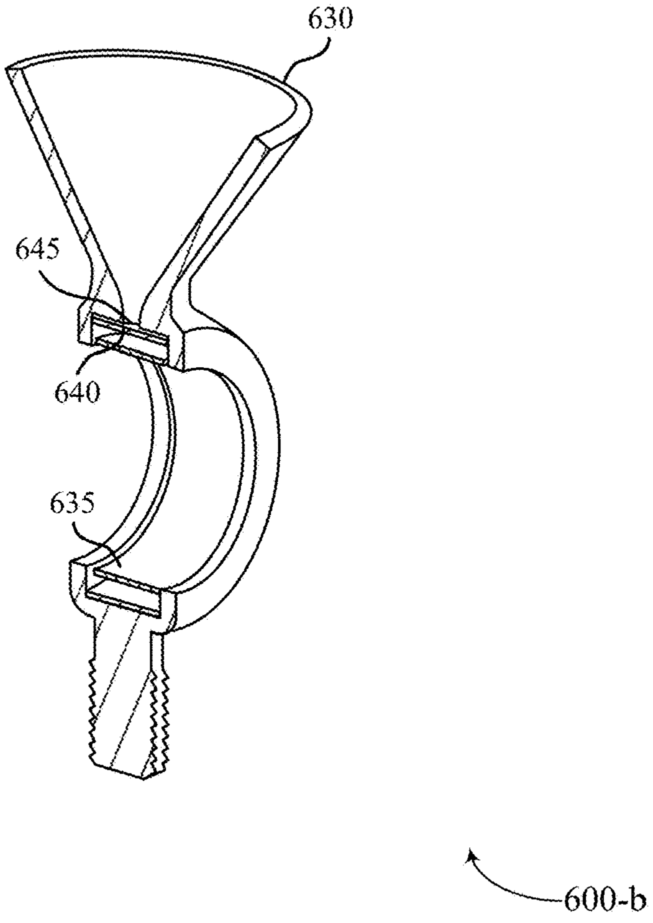

FIG. 6B illustrates an example of an outer aperture injection system 600-*b* that supports a process for manufacturing a wearable ring form factor in accordance with aspects of the present disclosure. The outer aperture injection system 600-*b* depicts a mold 630 in which a wearable ring device may be placed so that filler material may be injected into one or more cavities of the wearable ring device. By injecting the filler material into cavities of the wearable ring device, the wearable ring device may be sealed to prevent particles (e.g., liquids, dirt, and the like) from entering optical pathways of the wearable ring device, thereby preventing signal disturbances that may be caused by such particles.

As described with reference to FIGS. 3A, 3B, 4, 5A, 5B, and 6A the wearable ring device may include an inner ring-shaped housing 635, an outer ring-shaped housing 640, and a PCB coupled to the inner ring-shaped housing 635. However, the outer ring-shaped housing 640 may be different from the outer ring-shaped housing 610 described with reference to FIG. 6A in that the outer ring-shaped housing 640 may include an outer aperture 645 (e.g., additional aperture) within the outer circumferential surface of the outer ring-shaped housing 640. The outer ring-shaped housing 640 may be coupled to the inner ring-shaped housing 635, and a cavity may be defined by the outer ring-shaped housing 640 and the inner ring-shaped housing 635. In some examples, the outer ring-shaped housing 640 may be coupled to the inner ring-shaped housing 635 with a sealing material, sealing the cavity of the wearable ring device. Additionally, or alternatively, the outer ring-shaped housing 640 may be coupled to the inner ring-shaped housing 635 with a filler material.

In the outer aperture injection system 600-*b*, the wearable ring device may be placed within the mold 630 based on (e.g., after) coupling the outer ring-shaped housing 640 to the inner ring-shaped housing 635. When placing the wearable ring device within the mold 630, the wearable ring device may be positioned such that an outer aperture 645 of the outer ring-shaped housing 640 aligns with an opening of the mold 630 used to inject the filler material.

When the wearable ring device is placed and properly positioned within the mold 630, a filler material may be injected through the outer aperture 645 to fill at least a portion of the plurality of apertures of the inner ring-shaped housing 635. Additionally, or alternatively, the filler material may be injected through the outer aperture 645 to at least partially fill the cavity defined by the inner ring-shaped housing 635 and the outer ring-shaped housing 640. The filler material may be selected from a variety of materials enabling transmission of light (e.g., transparent or semi-transparent epoxy). Accordingly, sensors on the PCB within the wearable ring device may transmit and receive light through the filler material medium.

As described with reference to FIG. 6A, in some examples, the apertures of the inner ring-shaped housing 635 may be entirely filled with the filler material so that the filler material is flush with an inner circumferential surface of the inner ring-shaped housing 635. In other examples, the filler material may extend beyond an inner circumferential surface of the inner ring-shaped housing 635, in which cases the inner circumferential surface may be polished to remove excess filler material.

In some examples, the outer aperture 645 of the outer ring-shaped housing 640 may be filled with the material used to construct the outer ring-shaped housing 640 after injecting the filler material into the outer aperture 645. In other words, the outer aperture 645 may be filled to create a smooth and seamless outer surface of the wearable ring device. For instance, if the inner ring-shaped housing 635 is made from a first metallic material and the outer ring-shaped housing 640 is made from a second metallic material, the outer aperture 645 may be filled with the second metallic material after injecting the wearable ring device with the filler material. After filling the outer aperture 645 with the second metallic material, an outer circumferential surface of the outer ring-shaped housing 640 may be polished in order to smoothen the outer aperture 645 with the rest of the outer circumferential surface.

In additional or alternative implementations, techniques described herein may reduce (or eliminate) the need to polish the wearable device. For example, in some cases, filling the wearable device with the filler material through the outer aperture 645 may result in a smooth finish within and across the apertures of the ring-shaped housing, which may reduce or eliminate the need for polishing. Moreover, filling through the outer aperture 645 may result in a more uniform filler material within the apertures of the inner ring-shaped housing, which may thereby improve the optical performance of the wearable device.

Figure 7:
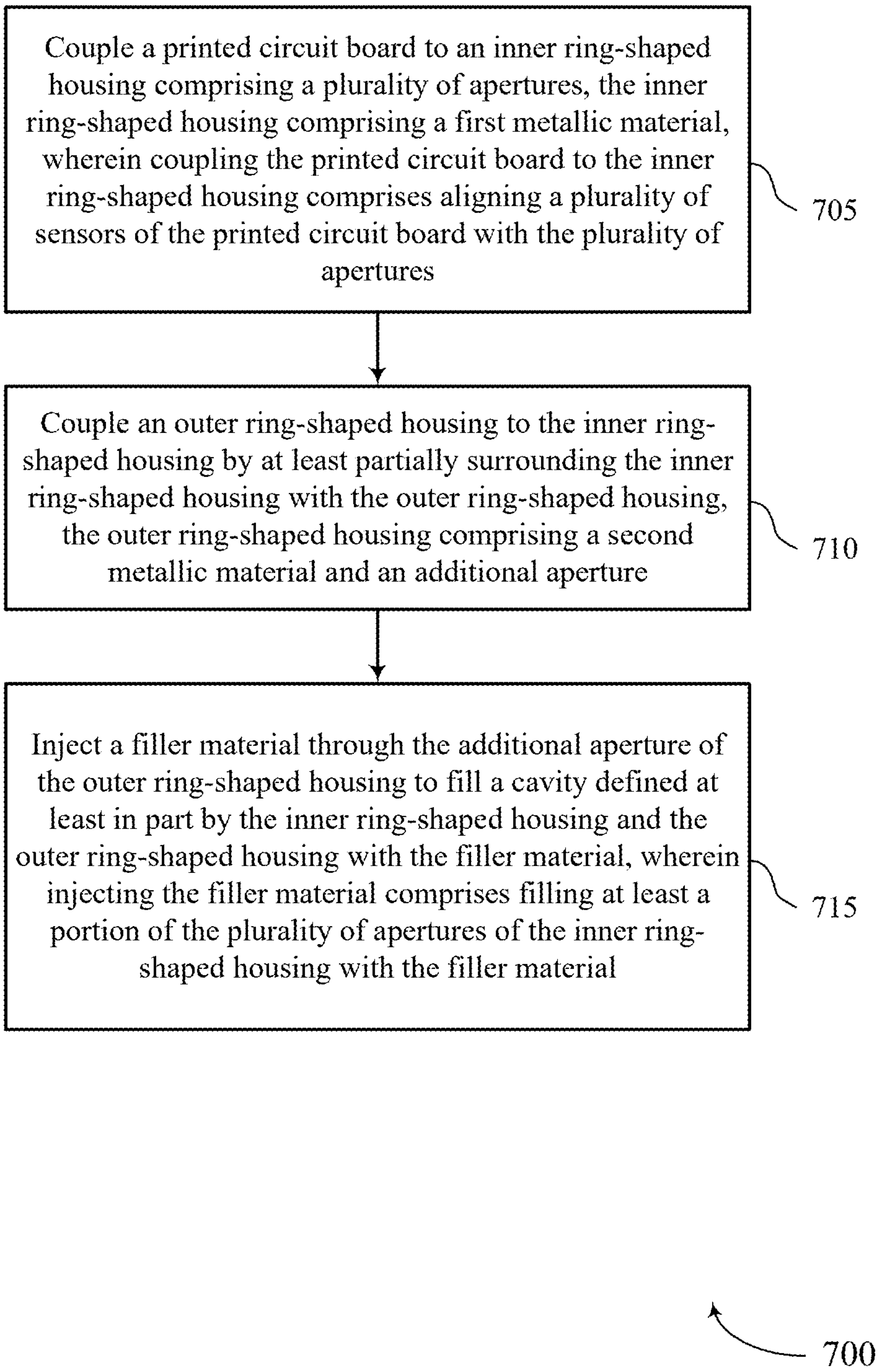
FIGS. 7 through 9 show flowcharts illustrating methods that support processes for manufacturing a wearable ring form factor in accordance with aspects of the present disclosure.

FIG. 7 shows a flowchart illustrating a method 700 that supports a process for manufacturing a wearable ring form factor in accordance with aspects of the present disclosure. The operations of the method 700 may be implemented by a wearable device manufacturer as described herein. For example, the operations of the method 700 may be performed by a wearable device manufacturer as described with reference to FIGS. 1 through 6B. In some examples, a wearable device manufacturer may execute a set of instructions to control the functional elements of the wearable device to perform the described functions. Additionally, or alternatively, the wearable device manufacturer may perform aspects of the described functions using special-purpose hardware.

At 705, the method may include coupling a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures. The operations of 705 may be performed in accordance with examples as disclosed herein. In some examples, aspects of the operations of 705 may be performed by a PCB coupling component.

At 710, the method may include coupling an outer ring-shaped housing to the inner ring-shaped housing by at least partially surrounding the inner ring-shaped housing with the outer ring-shaped housing, the outer ring-shaped housing comprising a second metallic material and an additional aperture. The operations of 710 may be performed in accordance with examples as disclosed herein. In some examples, aspects of the operations of 710 may be performed by an outer housing coupling component.

At 715, the method may include injecting a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material. The operations of 715 may be performed in accordance with examples as disclosed herein. In some examples, aspects of the operations of 715 may be performed by a filler injecting component.

Figure 8:
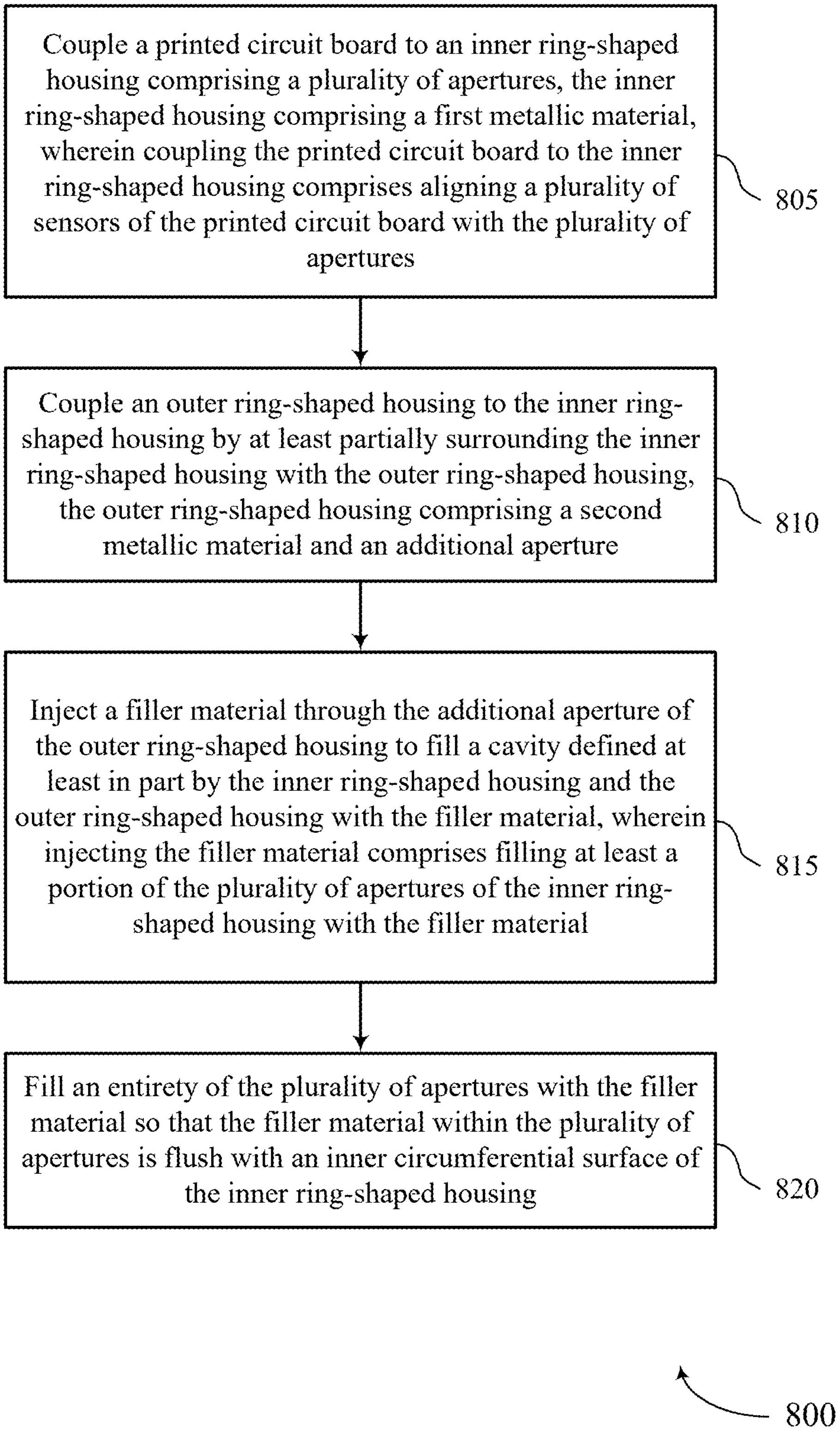

FIG. 8 shows a flowchart illustrating a method 800 that supports a process for manufacturing a wearable ring form factor in accordance with aspects of the present disclosure. The operations of the method 800 may be implemented by a wearable device manufacturer as described herein. For example, the operations of the method 800 may be performed by a wearable device manufacturer as described with reference to FIGS. 1 through 6B. In some examples, a wearable device manufacturer may execute a set of instructions to control the functional elements of the wearable device to perform the described functions. Additionally, or alternatively, the wearable device manufacturer may perform aspects of the described functions using special-purpose hardware.

At 805, the method may include coupling a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures. The operations of 805 may be performed in accordance with examples as disclosed herein. In some examples, aspects of the operations of 805 may be performed by a PCB coupling component.

At 810, the method may include coupling an outer ring-shaped housing to the inner ring-shaped housing by at least partially surrounding the inner ring-shaped housing with the outer ring-shaped housing, the outer ring-shaped housing comprising a second metallic material and an additional aperture. The operations of 810 may be performed in accordance with examples as disclosed herein. In some examples, aspects of the operations of 810 may be performed by an outer housing coupling component.

At 815, the method may include injecting a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material. The operations of 815 may be performed in accordance with examples as disclosed herein. In some examples, aspects of the operations of 815 may be performed by a filler injecting component.

At 820, the method may include filling an entirety of the plurality of apertures with the filler material so that the filler material within the plurality of apertures is flush with an inner circumferential surface of the inner ring-shaped housing. The operations of 820 may be performed in accordance with examples as disclosed herein. In some examples, aspects of the operations of 820 may be performed by a filler injecting component.

Figure 9:
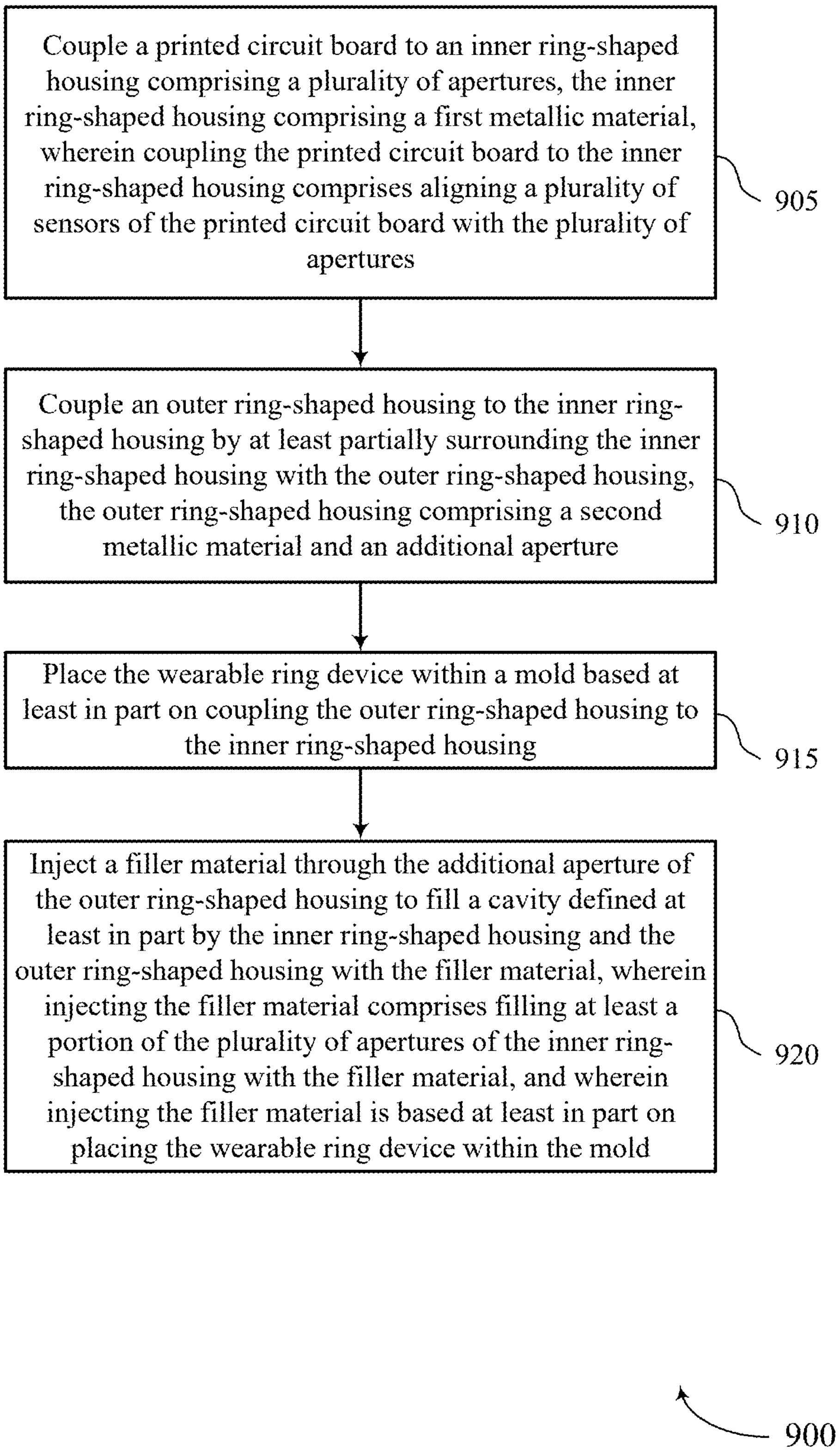

FIG. 9 shows a flowchart illustrating a method 900 that supports a process for manufacturing a wearable ring form factor in accordance with aspects of the present disclosure. The operations of the method 900 may be implemented by a wearable device manufacturer as described herein. For example, the operations of the method 900 may be performed by a wearable device manufacturer as described with reference to FIGS. 1 through 6B. In some examples, a wearable device manufacturer may execute a set of instructions to control the functional elements of the wearable device to perform the described functions. Additionally, or alternatively, the wearable device manufacturer may perform aspects of the described functions using special-purpose hardware.

At 905, the method may include coupling a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures. The operations of 905 may be performed in accordance with examples as disclosed herein. In some examples, aspects of the operations of 905 may be performed by a PCB coupling component.

At 910, the method may include coupling an outer ring-shaped housing to the inner ring-shaped housing by at least partially surrounding the inner ring-shaped housing with the outer ring-shaped housing, the outer ring-shaped housing comprising a second metallic material and an additional aperture. The operations of 910 may be performed in accordance with examples as disclosed herein. In some examples, aspects of the operations of 910 may be performed by an outer housing coupling component.

At 915, the method may include placing the wearable ring device within a mold based at least in part on coupling the outer ring-shaped housing to the inner ring-shaped housing. The operations of 915 may be performed in accordance with examples as disclosed herein. In some examples, aspects of the operations of 915 may be performed by a mold placing component.

At 920, the method may include injecting a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material, and wherein injecting the filler material is based at least in part on placing the wearable ring device within the mold. The operations of 920 may be performed in accordance with examples as disclosed herein. In some examples, aspects of the operations of 920 may be performed by a filler injecting component.

It should be noted that the methods described above describe possible implementations, and that the operations and the steps may be rearranged or otherwise modified and that other implementations are possible. Furthermore, aspects from two or more of the methods may be combined.

A method for manufacturing a wearable ring device is described. The method may include coupling a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures, coupling an outer ring-shaped housing to the inner ring-shaped housing by at least partially surrounding the inner ring-shaped housing with the outer ring-shaped housing, the outer ring-shaped housing comprising a second metallic material and an additional aperture, and injecting a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material.

An apparatus for manufacturing a wearable ring device is described. The apparatus may include a processor, memory coupled with the processor, and instructions stored in the memory. The instructions may be executable by the processor to cause the apparatus to couple a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures, couple an outer ring-shaped housing to the inner ring-shaped housing by at least partially surrounding the inner ring-shaped housing with the outer ring-shaped housing, the outer ring-shaped housing comprising a second metallic material and an additional aperture, and inject a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material.

Another apparatus for manufacturing a wearable ring device is described. The apparatus may include means for coupling a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures, means for coupling an outer ring-shaped housing to the inner ring-shaped housing by at least partially surrounding the inner ring-shaped housing with the outer ring-shaped housing, the outer ring-shaped housing comprising a second metallic material and an additional aperture, and means for injecting a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material.

A non-transitory computer-readable medium storing code for manufacturing a wearable ring device is described. The code may include instructions executable by a processor to couple a PCB to an inner ring-shaped housing comprising a plurality of apertures, the inner ring-shaped housing comprising a first metallic material, wherein coupling the PCB to the inner ring-shaped housing comprises aligning a plurality of sensors of the PCB with the plurality of apertures, couple an outer ring-shaped housing to the inner ring-shaped housing by at least partially surrounding the inner ring-shaped housing with the outer ring-shaped housing, the outer ring-shaped housing comprising a second metallic material and an additional aperture, and inject a filler material through the additional aperture of the outer ring-shaped housing to fill a cavity defined at least in part by the inner ring-shaped housing and the outer ring-shaped housing with the filler material, wherein injecting the filler material comprises filling at least a portion of the plurality of apertures of the inner ring-shaped housing with the filler material.

Some examples of the method, apparatuses, and non-transitory computer-readable medium described herein may further include operations, features, means, or instructions for filling an entirety of the plurality of apertures with the filler material so that the filler material within the plurality of apertures may be flush with an inner circumferential surface of the inner ring-shaped housing.

Some examples of the method, apparatuses, and non-transitory computer-readable medium described herein may further include operations, features, means, or instructions for filling the plurality of apertures with the filler material so that the filler material extends beyond an inner circumferential surface of the inner ring-shaped housing and polishing the inner circumferential surface of the inner ring-shaped housing so that the filler material may be flush with the inner circumferential surface of the inner ring-shaped housing.

Some examples of the method, apparatuses, and non-transitory computer-readable medium described herein may further include operations, features, means, or instructions for placing the wearable ring device within a mold based at least in part on coupling the outer ring-shaped housing to the inner ring-shaped housing, wherein injecting the filler material may be based at least in part on placing the wearable ring device within the mold.

In some examples of the method, apparatuses, and non-transitory computer-readable medium described herein, coupling the PCB to the inner ring-shaped housing may include operations, features, means, or instructions for engaging a first set of locating components of the inner ring-shaped housing with a second set of locating components of the PCB to maintain the PCB in a radial orientation of a plurality of radial orientations relative to the inner ring-shaped housing, wherein aligning the plurality of sensors of the PCB with the plurality of apertures may be based at least in part on the engaging.

In some examples of the method, apparatuses, and non-transitory computer-readable medium described herein, coupling the PCB to the inner ring-shaped housing may include operations, features, means, or instructions for sliding the PCB within a groove of the inner ring-shaped housing, wherein engaging the first set of locating components of the inner ring-shaped housing with the second set of locating components of the PCB may be based at least in part on the sliding.

In some examples of the method, apparatuses, and non-transitory computer-readable medium described herein, wherein the first set of locating components comprise one or more protrusions and wherein the second set of locking components comprise one or more grooves or detents and wherein the first set of locating components comprise the one or more grooves or detents and wherein the second set of locking components comprise the one or more protrusions.

In some examples of the method, apparatuses, and non-transitory computer-readable medium described herein, the outer ring-shaped housing may be coupled to the inner ring-shaped housing with a sealing material and the sealing material comprises an adhesive, a welding material, a compression fit component, or any combination thereof.

In some examples of the method, apparatuses, and non-transitory computer-readable medium described herein, the outer ring-shaped housing may be coupled to the inner ring-shaped housing based at least in part on the filler material.

In some examples of the method, apparatuses, and non-transitory computer-readable medium described herein, the filler material comprises a transparent epoxy material that may be configured to enable transmission of light through the plurality of apertures.

In some examples of the method, apparatuses, and non-transitory computer-readable medium described herein, the first metallic material of the inner ring-shaped housing may be the same as the second metallic material of the outer ring-shaped housing.

In some examples of the method, apparatuses, and non-transitory computer-readable medium described herein, the first metallic material of the inner ring-shaped housing may be different from the second metallic material of the outer ring-shaped housing.

In some examples of the method, apparatuses, and non-transitory computer-readable medium described herein, the PCB comprises a flexible PCB.

Some examples of the method, apparatuses, and non-transitory computer-readable medium described herein may further include operations, features, means, or instructions for filling the additional aperture of the outer ring-shaped housing with the second metallic material based at least in part on filling at least the portion of the plurality of apertures of the inner ring-shaped housing with the filler material and polishing an outer circumferential surface of the outer ring-shaped housing based at least in part on filling the additional aperture with the second metallic material.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for manufacturing a wearable ring device, comprising:

coupling a printed circuit board to a first portion of the wearable ring device, the first portion of the wearable ring device comprising at least one aperture, wherein coupling the printed circuit board to the first portion of the wearable ring device comprises aligning at least one sensor of the printed circuit board with the at least one aperture;

coupling a second portion of the wearable ring device to the first portion of the wearable ring device by at least partially surrounding the first portion of the wearable ring device with the second portion of the wearable ring device; and injecting a filler material through one or more apertures of the at least one aperture of the first portion of the wearable ring device to fill a cavity, defined at least in part by the first portion of the wearable ring device and the second portion of the wearable ring device, with the filler material.

2. The method of claim 1, further comprising:

filling an entirety of the at least one aperture with the filler material so that the filler material within the at least one aperture is flush with an inner surface of the first portion of the wearable ring device.

3. The method of claim 1, further comprising:

filling the at least one aperture with the filler material so that the filler material extends beyond an inner surface of the first portion of the wearable ring device; and polishing the inner surface of the first portion of the wearable ring device so that the filler material is flush with the inner surface of the first portion of the wearable ring device, an outer surface of the second portion of the wearable ring device, or both.

4. The method of claim 1, further comprising:

placing the wearable ring device within a mold based at least in part on coupling the second portion of the wearable ring device to the first portion of the wearable ring device, wherein the filler material is injected based at least in part on placing the wearable ring device within the mold.

5. The method of claim 1, wherein coupling the printed circuit board to the first portion of the wearable ring device comprises:

engaging a first set of locating components of the first portion of the wearable ring device with a second set of locating components of the printed circuit board to maintain the printed circuit board in a radial orientation of a plurality of radial orientations relative to the first portion of the wearable ring device, wherein aligning the at least one sensor of the printed circuit board with the at least one aperture is based at least in part on the engaging.

6. The method of claim 5, wherein coupling the printed circuit board to the first portion of the wearable ring device comprises:

sliding the printed circuit board within a groove of the first portion of the wearable ring device, wherein engaging the first set of locating components of the first portion of the wearable ring device with the second set of locating components of the printed circuit board is based at least in part on the sliding.

7. The method of claim 5, wherein the first set of locating components comprise one or more protrusions and wherein the second set of locating components comprise one or more grooves or detents, or wherein the first set of locating components comprise the one or more grooves or detents and wherein the second set of locating components comprise the one or more protrusions.

8. The method of claim 1, wherein the first portion of the wearable ring device is coupled to the second portion of the wearable ring device with a sealing material, wherein the sealing material comprises an adhesive, a welding material, a compression fit component, or any combination thereof.

9. The method of claim 1, wherein the first portion of the wearable ring device is coupled to the second portion of the wearable ring device based at least in part on the filler material.

10. The method of claim 1, wherein the filler material comprises a transparent epoxy material that enables transmission of light through the at least one aperture.

11. The method of claim 1, wherein the first portion of the wearable ring device comprises a first metallic material, and wherein the second portion of the wearable ring device comprises a second metallic material.

12. The method of claim 11, wherein the first metallic material of the first portion of the wearable ring device is the same as the second metallic material of the second portion of the wearable ring device.

13. The method of claim 11, wherein the first metallic material of the first portion of the wearable ring device is different from the second metallic material of the second portion of the wearable ring device.

14. The method of claim 1, wherein the printed circuit board comprises a flexible printed circuit board.

15. The method of claim 1, wherein the first portion of the wearable ring device is welded to the second portion of the wearable ring device.

* * * * *